(12) United States Patent
Chen et al.

(10) Patent No.: US 8,940,865 B2
(45) Date of Patent: Jan. 27, 2015

(54) MYOCARDIAL PEPTIDE, PREPARATION METHOD AND USES THEREOF

(75) Inventors: Yusong Chen, Liaoning (CN); Shu Li, Liaoning (CN); Risheng Wang, Liaoning (CN); Qiang Liang, Liaoning (CN); Zheng Zeng, Liaoning (CN); Xiaohong Qian, Liaoning (CN); Dong Cao, Liaoning (CN); Huimin Liang, Liaoning (CN)

(73) Assignee: Dalian Zhen-Ao Pharmaceutical Co, Ltd., Dalian (CN)

( * ) Notice: Subject to any disclaimer, the term of this patent is extended or adjusted under 35 U.S.C. 154(b) by 831 days.

(21) Appl. No.: 13/054,229

(22) PCT Filed: Jul. 15, 2008

(86) PCT No.: PCT/CN2008/071647
§ 371 (c)(1),
(2), (4) Date: Mar. 18, 2011

(87) PCT Pub. No.: WO2010/006476
PCT Pub. Date: Jan. 21, 2010

(65) Prior Publication Data
US 2011/0160432 A1    Jun. 30, 2011

(51) Int. Cl.
*C07K 7/00* (2006.01)

(52) U.S. Cl.
USPC .......... 530/326; 530/328; 530/334; 514/21.5; 514/21.6

(58) Field of Classification Search
USPC ................. 530/326, 328, 334; 514/21.5, 21.6
IPC ............................... C07K 7/00,7/06, 7/08, 1/04
See application file for complete search history.

(56) References Cited

U.S. PATENT DOCUMENTS 6,013,858 A * 1/2000 Wallace et al. ................. 800/18
2007/0117745 A1   5/2007 Chen et al.

OTHER PUBLICATIONS

International Search Report (PCT/ISA/210) issued on Apr. 23, 2009, by Chinese Patent Office as the International Searching Authority for International Application No. PCT/CN2008/071647.

* cited by examiner

*Primary Examiner* — David Lukton
(74) *Attorney, Agent, or Firm* — Buchanan Ingersoll & Rooney PC (57) ABSTRACT

Disclosed are two myocardial peptides, whose amino acid sequences are Trp-Ser-Asn-Val-Leu-Arg-Gly-Met-Gly-Gly-Ala-Phe and Lys-Gly-Ala-Trp-Ser-Asn-Val-Leu-Arg-Gly-Met-Gly-Gly-Ala-Phe respectively, wherein the latter can be obtained by extracting from myocardial peptides solution. The myocardial peptides can be used in the produce of a medicament for preventing and/or treating myocardial ischemia.

12 Claims, 8 Drawing Sheets

MYOCARDIAL PEPTIDE, PREPARATION METHOD AND USES THEREOF

This application is national stage entry of PCT/CN2008/071647, filed Jul. 15, 2008.

TECHNICAL FIELD

The present invention relates to a polypeptide substance, specifically relates to two active polypeptides, the preparation method and the use thereof.

BACKGROUND OF THE INVENTION

"The protection of myocardium" is a hot subject in the research of the cardiology and cardiac surgery. The latest information indicates that the myocardium cell would take place change in the condition of ischemia and hypoxia, such as intra-cellular over-loading of the calcium, generation of free group, damage of the cell membrane, decline of the ATP (adenosine triphosphate) level, exhaustion of the oxygen, etc.

In order to interfere the myocardial ischemia and protect myocardium, many drugs were developed in recent 20 years, e.g. β-receptor antagonist, calcium antagonist, transferase inhibitor, many kinds of free group scavenger, etc., whose protection effect on the myocardium cell in clinic is not affirmed yet. None of the existing medicine for treatment of ischemia myocardial can absolutely decreases the myocardial infarction and antagonizes the myocardial ischemia.

The available cardiovascular drugs, except for converting enzyme inhibitor that has the function of blocking the generation of growth factors, inhibiting protein synthesis and myocardial hypertrophy, do not have the function of regulating the growth, differentiation and rehabilitation of myocardium. In recent years, pharmacological treatment is emphasized overseas to induce the protection of myocardium cells themselves, such as promoting the myocardial regeneration by transduction gene etc, cardiotrophin and myotrophin. Moreover, extracellular signals are used to trigger various transmission mechanism to regulate the proliferation or reconstitution of myocardial and vascular cells. But all these researches are at the stage of animal test or preclinical study.

It is clearly demonstrated from the above studies that, in the situation that protection of myocardium by extracorporeal circulation is not consummated yet, it is necessary to provide a drug which can protect myocardium before, during or after surgery without any damage to the organism, interventions, which is important for exploring the prevention and cure of myocardial ischemia and reperfusion.

ZL94102798 discloses a growth-stimulation peptide of myocardial cells and the preparation method thereof. The process comprises the steps of: crushing the heart of healthy infant mammals other than a human with mechanical means, deeply freezing at −20° C. and heating to 60~100° C. after being dissolved in water, then deeply freezing at −20° C. and centrifugating at 3000 rpm after being dissolved, and finally obtaining a polypeptide active substance with molecular weight less than 20000 Da through negative pressure interception column, sterilization, split charging, lyophilization and packing.

ZL94102799 discloses a growth-stimulating peptide of myocardial(GMGSP) that can stimulate DNA synthesis and protein synthesis of primarily cultured myocardial cells and that is isolated from the heart of healthy infant mammal. GMGSP is stable at PH 2~9 and its biological activity does not change when being heated at 95~100° C. for 10 minutes or at 60~70° C. for 30 minutes; its biological activity is lost when being placed in proteolytic enzymes at 37° C. for 2 hours. A polymer is formed at 22° C.~30° C. in aqueous solution without obviously changing in biological activity; biological activity does not change if GMGSP is lyophilized and sealed with 3%~8% mannitol and stored at room temperature for 1.5 years, or at 4° C. for 2 years, or at −20° C. for 3 years. HPLC analysis indicates that the GMGSP is composed of 4 components each having biological activity, the relative peaks and retention times of which are 10.4% (2.88 min), 6.4% (3.93 min), 36.3% (5.09 min) and 7.3% (7.41 min), respectively. The molecular weight of two bands shown by SDS-PAGE analysis are respectively 8500 Da and 10800 Da, the average number molecular weight shown by HPLC analysis is 9800 Da and weight average molecular weight is 10500 Da, and both components have biological activity.

Chinese patent 03141352.8 with title of "cardio myopeptidin and the use thereof" discloses a cardio myopeptidin isolated from the heart of healthy infant mammal with the weight average molecular weight of less than 10000 Da, wherein the content of peptide is 75%~90%; the content of free amino acid is 6%~15%; the content of RNA is 1~2%; the content of DNA is 3~7%. It also discloses an use of the cardio myopeptidin for producing the medicament for treatment of cardiovascular disease and reperfusion injury. Chinese patent 03137133.7 discloses a preparation method of cardio myopeptidin, which comprises the steps of: cleaning and cutting the ventricle muscle of hearts of healthy non-human mammals, adding sterile distilled water and homogenizing, repeatedly freezing and thawing the homogenate for 3-4 times; heating to 65~90° C. to remove the residue, filtering by the plate-and-frame filter to get a coarse filtrate, ultra-filtering the coarse filtrate with a hollow-fiber column to get a refined filtrate; ultra-filtering the refined filtrate by ultrafiltration membrane to intercept the cardio myopeptidin solution with the molecular weight less than 10000 Da; concentrating the solution by reverse osmosis, obtaining the product after filtration sterilization and lyophilization.

Above-mentioned study results indicate that the cardio myopeptidin, which contains several active contents, such as polypeptide, free amino acid, DNA etc, is isolated from the heart of healthy infant mammal other than a human mammal.

The polypeptides are linear chain protein compounds which are composed of various amino acids arranged in different sequence. These compounds always have strong physiological activity and functional specificity. Therefore, those polypeptides have a wide use for producing medicament for treatment of various diseases.

So far, there are no patents or documents disclosing the sequence and the use of polypeptides in cardio myopeptidin.

SUMMARY OF THE INVENTION

The first object of the present invention is to provide two polypeptides, one of which has the sequence encoded by SEQ ID NO: 1, the molecular weight of 1294.75 (abbr. cardio myopeptidin X);

SEQ ID NO: 1:
Trp-ser-asn-val-leu-Arg-gly-met-gly-gly-ala-phe.

The cardio myopeptidin X is connected with Ala, Gly and Lys in turn on the one end-point ending up with Trp to form a new polypeptide (abbr. cardio myopeptidin C) with sequence encoded by SEQ ID NO: 2 and the molecular weight of 1550.91, SEQ ID NO: 2:
lys-gly-ala-Trp-ser-asn-val-leu-Arg-gly-met-gly-gly-ala-phe.

The polypeptides are extracted from cardio myopeptidin solution, and are found have activity through determination. The polypeptides have prominent effect on produce of medicament for prevention and/or treatment of myocardial ischemia, cerebral ischemia, hepatic ischemia, intestines ischemia, stomach ischemia, lung ischemia or nephridium ischemia.

To achieve the objects, the technical solution of present invention is as follows:

A polypeptide, wherein amino acid sequence of the polypeptide is encoded by Trp-Ser-Asn-Val-Leu-Arg-Gly-Met-Gly-Gly-Ala-Phe.

One end-point of polypeptide being linked with Trp, connects Ala, Gly and Lys in turn, and the amino acid sequence is encoded by Lys-Gly-Ala-Trp-Ser-Asn-Val-Leu-Arg-Gly-Met-Gly-Gly-Ala-Phe.

The second object of the present invention is to provide a process for the preparation of the cardio myopeptidin C.

To achieve above objects, the technical solution of present invention is as following:

A method for extracting the myopeptidin C from cardio myopeptidin solution, comprising the steps of:

(1) adding ammonium sulphate solution to the cardio myopeptidin solution, depositing, centrifugating, separating supernatant fluid and sediment;

(2) filtrating the supernatant fluid by solid phase extraction tube with organic solvent as eluent, collecting fraction A;

(3) concentrating the fraction A then being isolated by reversion phase preparative chromatography, collecting active fraction B;

(4) concentrating the active fraction B, then being further isolated by analytical type reversion phase chromatography, collecting active fraction C;

(5) detecting the fraction C with mass spectrometric detection to identify amino acid sequence of the active polypeptide in active fraction C by MS data analysis, the active fraction C being the polypeptide.

In the invention, weight percent concentrations of the ammonium sulphate solution is 60 to 80%, preferably 70%.

In the invention, the organic solvent in step (2) is the mixture comprising acetonitrile 60% and trifluoroacetic acid 0.1%.

In step (3) of the invention, fraction A is concentrated to ⅛~¾ of the original volume, and the condition of the reversion phase preparative chromatography is: mobile phase: A phase being 100% $H_2O$+0.1% TFA, B phase being 60% ACN+0.1% TFA; ultraviolet detector: wavelength $\lambda$=280 nm, R=3.0; gradient elution: 0~5 Min 0% B, 5~35 min 0%~100% B, 35~40 min 100% B, 40~45 min 100%~0% B.

In step (4) of the invention, the fraction B is concentrated to ⅛~½ of the original volume, and the condition of further separation by using the analytical type reversion phase chromatography is: mobile phase: A phase being 100% $H_2O$+0.1% TFA, B phase being 95% ACN+0.1% TFA; ultraviolet detector: wavelength $\lambda$=280 nm, R=3.0; gradient elution: 0~5 Min 0% B, 5~50 min 0%~100% B, 35~40 min 100% B, 40~45 min 100%~0% B.

The cardio myopeptidin solution of the invention contains the polypeptide solution isolated from the heart of healthy mammal other than a human mammal, wherein the content of peptide is 75%~90%, the content of free amino acid is 6%~15%, the content of RNA is less than 2%, content of DNA is less than 7%, and molecular weight is less than 10000 Da. The cardio myopeptidin solution also can be the existing product of cardio myopeptidin.

Another object of the invention is to provide a chemical synthesis method for the preparation of the cardio myopeptidin C.

To achieve the object, the technical solution of present invention is as follows:

A chemical synthesis method of the cardio myopeptidin C, wherein the method comprises the steps of:

(1) protecting the amino-group of tryptophane, serine, aspartic acid, valine, leucine, arginine, glycine, methionine, alanine, phenylalanine and lysine by using protecting group for amino-group respectively;

(2) swelling solid phase carrier, combining the first protected amino acid of SEQ ID:1 onto the solid phase carrier, then rinsing the combined product, obtaining solid phase carrier onto which the first protected amino acid combines;

(3) adding the second amino acid of SEQ ID NO:1 to the solid phase carrier being combined with the first protected amino acid to form the peptide linkage in presence of condensating agent, then removing the protecting group for amino-group from the amino acid, rinsing to obtain the solid phase carrier;

(4) according to the sequencing amino acid of SEQ ID NO:1, adding corresponding protected amino acid in turn, repeating the steps of removing amino group protecting group and rinsing to extend the peptide chain until the last amino acid is linked to the peptide chain;

(5) immersing the solid phase carrier being combined with polypeptide prepared in step (4) in soak solution, then filtering and depositing the filtrate to obtain coarse polypeptide;

(6) isolating and purifying the coarse polypeptide to obtain target product.

In step (1) of the invention, the amino-group is protected by following groups:

(1) carbobenzoxyl (2) t-butyloxycarbonyl (3) tosyl (4) fmoc:9-fiuorenylmethoxycarbonyl.

In nature, each polypeptide or protein is polymerized by free amino acid through peptide bond. In the process of translation of the protein, the polypeptide chain is extended from amino-end (N-end) to carboxyl-end (C-end). In the beginning of the chemical synthesis, the first amino acid of the carboxyl-end (C-end) is combined on the activated resin, then the amino group protecting group is removed, and the second amino acid of the carboxyl-end is added into the reactor to form the peptide bond by reaction of the two amino acids. The third amino acid, the forth amino acid and so on are added according the sequence of arrangement of amino acids, until the last amino acid is combined to polypeptide.

Another object of the present invention is to provide the use of cardio myopeptidin C for producing medicament for the prevention and/or treatment of ischemia of tissue and organ, preferably the use of the polypeptide for producing medicament for the prevention and/or treatment of myocardial ischemia, cerebral ischemia, hepatic ischemia, intestines ischemia, stomach ischemia, lung ischemia or nephridium ischemia, more preferable the use of the polypeptide for producing medicament for the prevention and/or treatment of myocardial ischemia.

The invention discloses two kinds of extraction methods, and two kinds of polypeptides extracted from cardio myopeptidin solution and the sequence thereof, also discloses chemical synthesis, purify, activity determination and identification of the two kinds of polypeptides. The invention has following advantage: the two polypeptides are indicated by activity determination to have activities; the polypeptides are indicated by animal experiments and clinical experiments that the polypeptides have remarkable effect on production of medicament for treatment of myocardial ischemia, cerebral ischemia and hepatic ischemia. At the same time, the two kinds of polypeptides have the characteristics of definite structure, high activity, easiness of production, low cost and that its mechanism is easy to be explained, etc.

BRIEF DESCRIPTION OF THE DRAWINGS

FIG. 7 indicates the effect of protective administration of myopeptidin C to the size of myocardial infarction area of hypoxia/reoxygenation injury rat, FIG. 7-a is Sham Operation Group, FIG. 7-b is Model Group, FIG. 7-c is Positive Control Group, FIG. 7-d is CMPC group;

FIG. 8 indicates the effect of therapeutic administration of myopeptidin C to the size of myocardial infarction area of hypoxia/reoxygenation injury rat, FIG. 8-a is Sham Operation Group, FIG. 8-b is Model Group, FIG. 8-c is Positive Control Group, FIG. 8-d is CMPC group;

DETAILED DESCRIPTION

Example 1

This example relates the synthesis of cardio myopeptidin C.

The amino acid sequence of the polypeptide is: Lys-Gly-Ala-Trp-Ser-Asn-Val-Leu-Arg-Gly-Met-Gly-Gly-Ala-Phe.

1. Synthesis: First, protecting the amino-group of amino acid contained in the polypeptide by using amino-group protecting group (9-fluorenylidene carbomethoxy), (has dosage of 20~100 gram/gram), then swelling the wang resin by chlorethyl ether with the dosage of 50~100 ml/g; adding the first amino acid into the resin to combine the amino acid onto the resin. After rinsing the resin with methylene dichloride, removing the amino-group protecting group by hexahydropyridine (has dosage of 10~80%, preferably of 20~40%). At the same time, the second amino acid being added to the resin combined with the first amino acid after being activated by HBTU (2-(1H-Benzotriazole-1-yl)-1,1,3,3-tetramethyluronium hexafluorophosphate) and being neutralized by N,N-Diisopropylethylamine, to form the peptide bond after the reaction of the two amino acid. Then according the sequence of animo acid, adding corresponding amino acid, and repeating the steps of rinsing, removing amino-group protecting group and activating the carboxyl etc for 14 times to extend peptide chain, until the last amino acid unite is combined to the chain. After synthesis, the polypeptide being combined with the resin, which are separated from each other by separating liquid, selected from phenol, thioanisole, trifluoroacetic acid (TFA) or mixture thereof. filtrate of mixture of polypeptide is obtained after soaking the resin connected with the polypeptide (II) with 10~80 ml separating liquid, stirring for 1.5 hours at room temperature, and then filtering. The free polypeptide substance being separated by adding a ether and depositing. The separated polypeptide being dissolved in water or alkali solution (selected from: ammonium hydrogen carbonate, ammonium carbonate, sodium carbonate, sodium bicarbonate), and then obtaining the purified polypeptide substance by general liquid chromatography (LC). Measuring the concentration of purified polypeptide substance by ultraviolet spectrophotometric, and the polypeptide substance being examined by the mass spectrometric analysis.

Example 2

This example relates to the synthesis of cardio myopeptidin X.

The amino acid sequence of the polypeptide is: Trp-Ser-Asn-Val-Leu-Arg-Gly-Met-Gly-Gly-Ala-Phe.

The method is the same as that described in Example 1.

Example 3

This example relates to the synthesis of cardio myopeptidin C.

The amino acid sequence of the polypeptide is: Lys-Gly-Ala-Trp-Ser-Asn-Val-Leu-Arg-Gly-Met-Gly-Gly-Ala-Phe.

The method contains following steps:

(1) removing of the amino-group protecting group Fmoc: taking Fmoc-Lys-CLTR resin, soaking and rinsing for 3 times by methylene dichloride with 2 minutes every time, then draining, adding 10 ml methylene dichloride solution containing 50% piperidine at room temperature, draining after reacting for 5 minutes, adding the same solution and reacting for 30 min, then draining, rinsing respectively with 8 ml~10 ml methylene dichloride, ethanol, and methylene dichloride in turn, draining, determining the total amino content by taking a small amount of resin (2 mg~10 mg) through salicylal free group quantitative determination.

(2) forming of peptide bond (DCC-HOBt condensation method): adding methylene dichloride containing Fomc-Gly (t-Bu) and methylene dichloride containing 1-hydroxy benzotriazole, at the same time adding dimethyl formamide for assistant dissolving for 30 min, then adding 2 ml methylene dichloride containing N,N'-dicyclohexylcarbodiimide to react overnight at 20, draining and rinsing to get the resin linked with peptide Fmoc-Gly(t-Bu)-Lys(Boc)-R. Drying a small amount of resin to a constant weight, determining the total amino content by using salicylal free group quantitative determination, therefore, the condensation rate is calculated. In the process of reaction, monitoring the process by ninhydrin color reaction, with the phenomenon of that the resin is transparent and colourless when the condensation reaction is over.

(3) acetylizing of the unreacted amino group: adding the resin linked with peptide preparing in the step (2) to pyridine containing 50% acetic anhydride at room temperature, rinsing and draining, then repeating the process with the same solution to acetylize the unreacted amino group.

(4) replacing Fmoc-Lys(Boc)-wang-R in step (1) with Fmoc-Gly(t-Bu)-Lys(Boc)-R, replacing Fmoc-Gly(t-Bu) in step (2) with Fmoc-Ala(Trt), repeating the process of step (1)~(3), repeating in turn, using the resin linked with peptide synthesized in previous step as amino component of next step, to carry out the reactions for 14 times until the bonds between the 15 amino acids are all formed.

(5) removing of the lateral chain protecting group and resin combined with the polypeptide: adding 30 ml methylene dichlorideand and 3.0 ml TFA to the resin linked with polypeptide containing 12 amino acids, to react for 30 minutes at room temperature, filtering, keeping the filtrate. Adding 10 ml methylene dichlorideand containing 50% TFA to the filtrate, reacting for 20 minutes, rinsing for 3 times with fore said solution, combining the rinse solution and the fore filtrate, vaporizing to a small amount of residue by revolving evaporimeter, adding abundant anhydrous aether to precipitate white powdered substance, removing the liquid phase by centrifugation, grinding the powder for 5 times by using anhydrous aether, then vacuum drying, weighting and calculating the production rate;

(6) taking a small mount of product to take an electrophoresis detection and RP-HPLC analysis with the RP-HPLC condition of: Alltech Platinum C18 chromatographic column; buffer A of water solution containing 0.1% trifluoroacetic acid (TFA); buffer B of water solution containing 0.1% TFA and 90% acetonitrile (all volume percent); gradient elution with that volume percent of buffer B is rised from 10% to 50% in 40 minutes, the velocity of mobile phase of 1.0 ml/min, detection wavelength of 214 nm.

Example 4

This example relates to the synthesis of cardio myopeptidin X.

The amino acid sequence of the polypeptide is: Trp-Ser-Asn-Val-Leu-Arg-Gly-Met-Gly-Gly-Ala-Phe.

The method is the same as that described in Example 3.

Example 5

This example relates to the synthesis of cardio myopeptidin C.

The method contains the steps as following:

(1) Instruments and Equipments

Elite high pressure liquid chromatography P230 system; FP-2 two-dimensional liquid chromatography separation system analysis type chromatographic column (from DIONEX company of US); C18 column 4.6×250 mm (from waters company), SPE solid-phase extraction column (from waters company); C18 semi-preparative reverse column (Thermo Electron Corporation); vacuum frozen dryer (Thermo Electron Corporation), centrifuger, etc.

Figure 1:
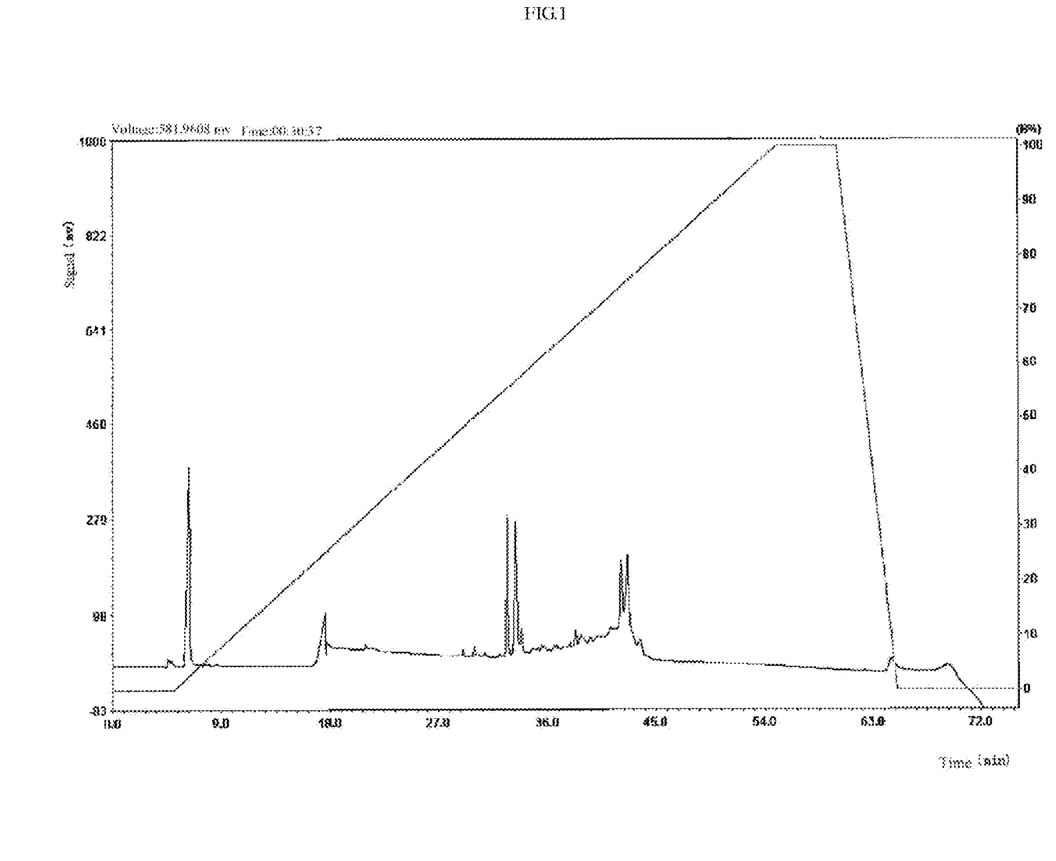
FIG. 1 shows a mass-spectrogram of cardio myopeptidin X with molecular weight of 1294.75 (4700MS/MS Procursor 1294.75 spec#1MC[BP=1147.4,4886])
Figure 2:
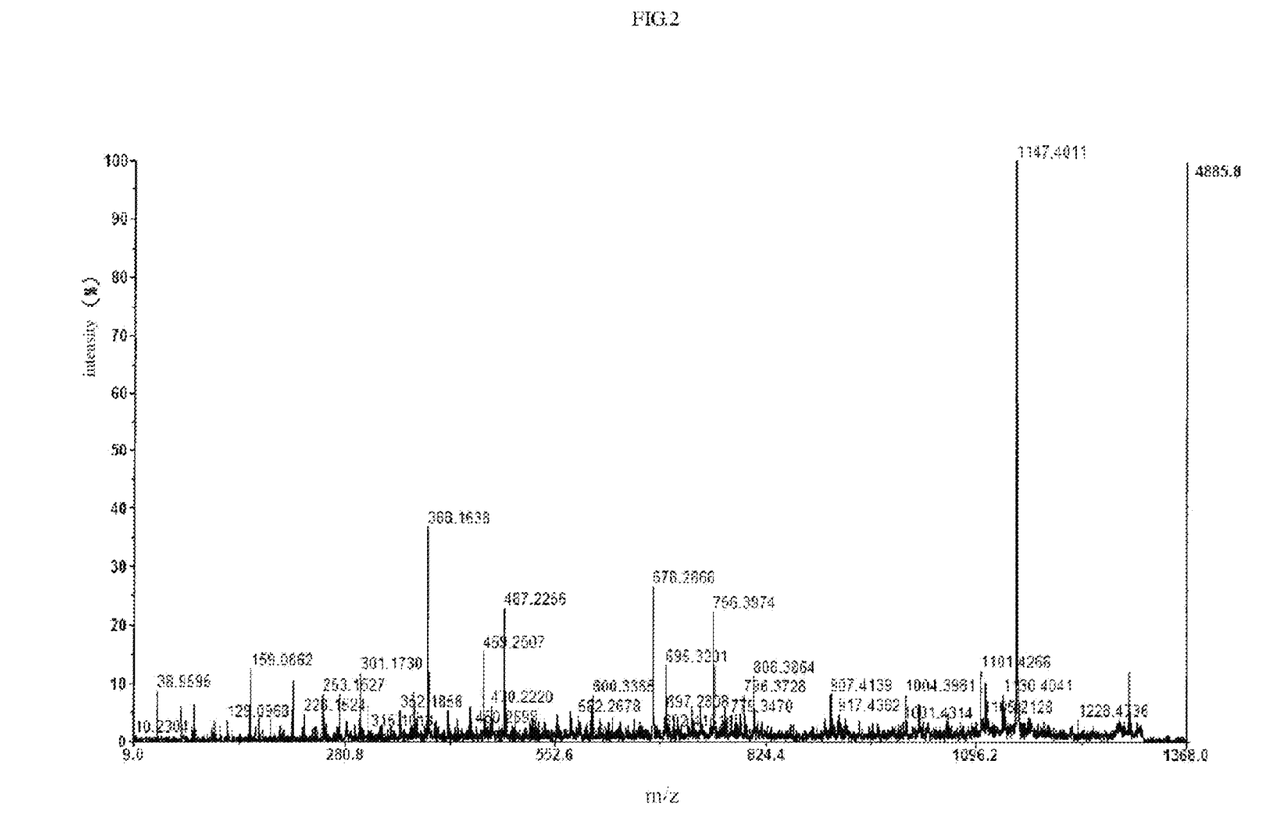
FIG. 2 shows a mass-spectrogram of cardio myopeptidin C with molecular weight of 1550.91 (4700MS/MS Procursor 1550.91 spec#1MC[BP=1403.5,3630])
Figure 3:
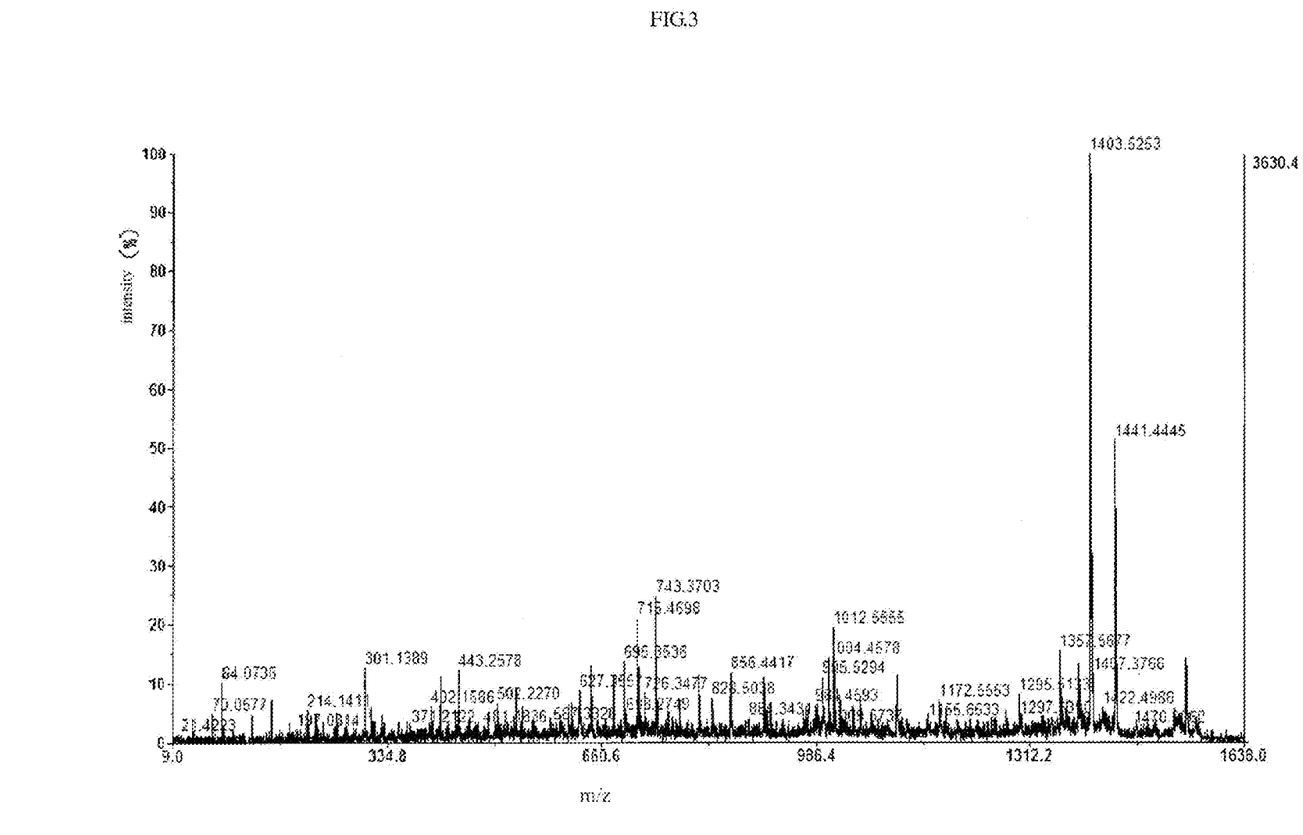
FIG. 3 shows MS/MS denovo sequence matching KGAW-SNVLRGMGGAF of cardio myopeptidin C with molecular weight of 1550.91
Figure 4:
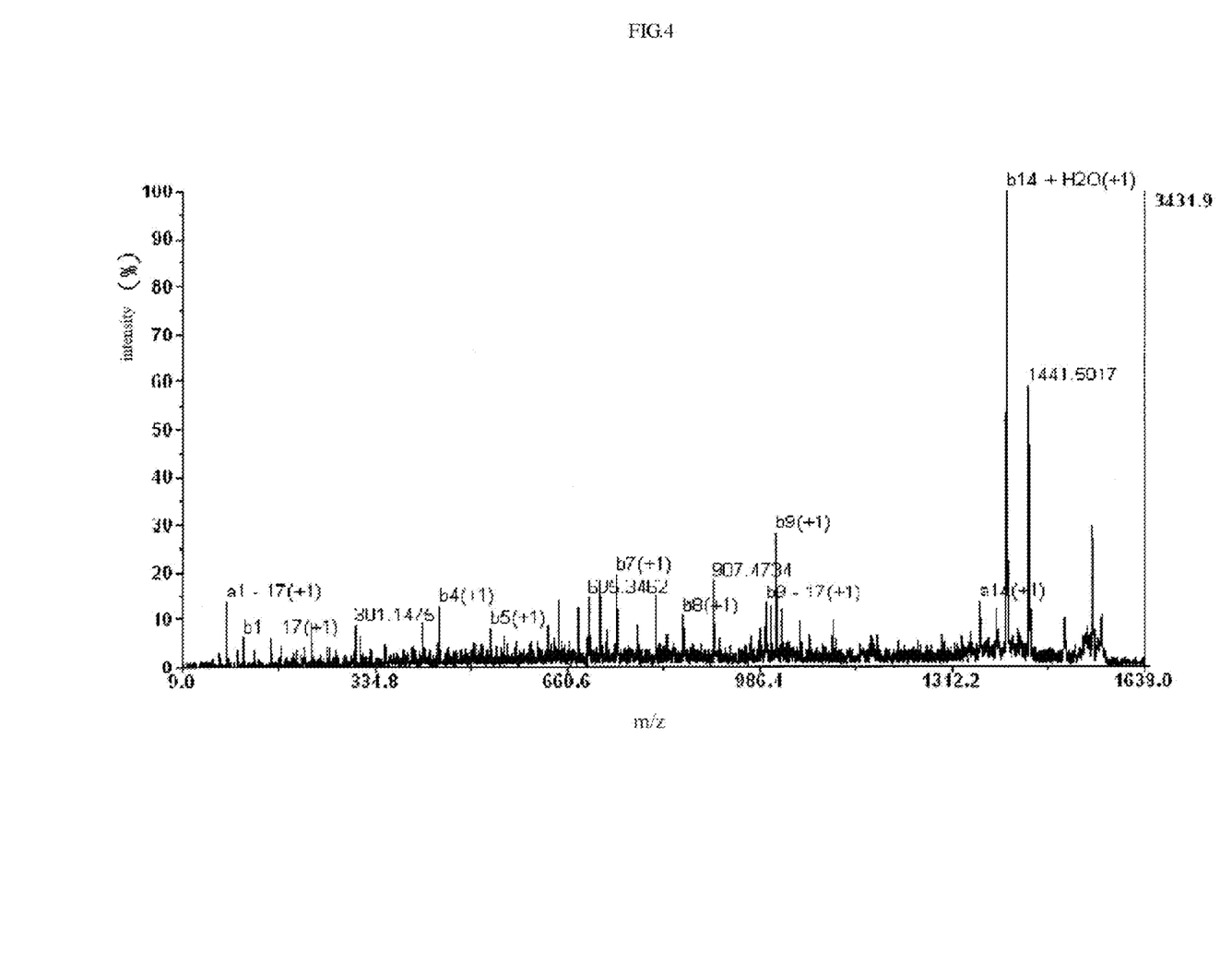
FIG. 4 shows MS/MS denovo sequence matching WSNV-LRGMGGAF of cardio myopeptidin X with molecular weight of 1294.75.
Figure 5:
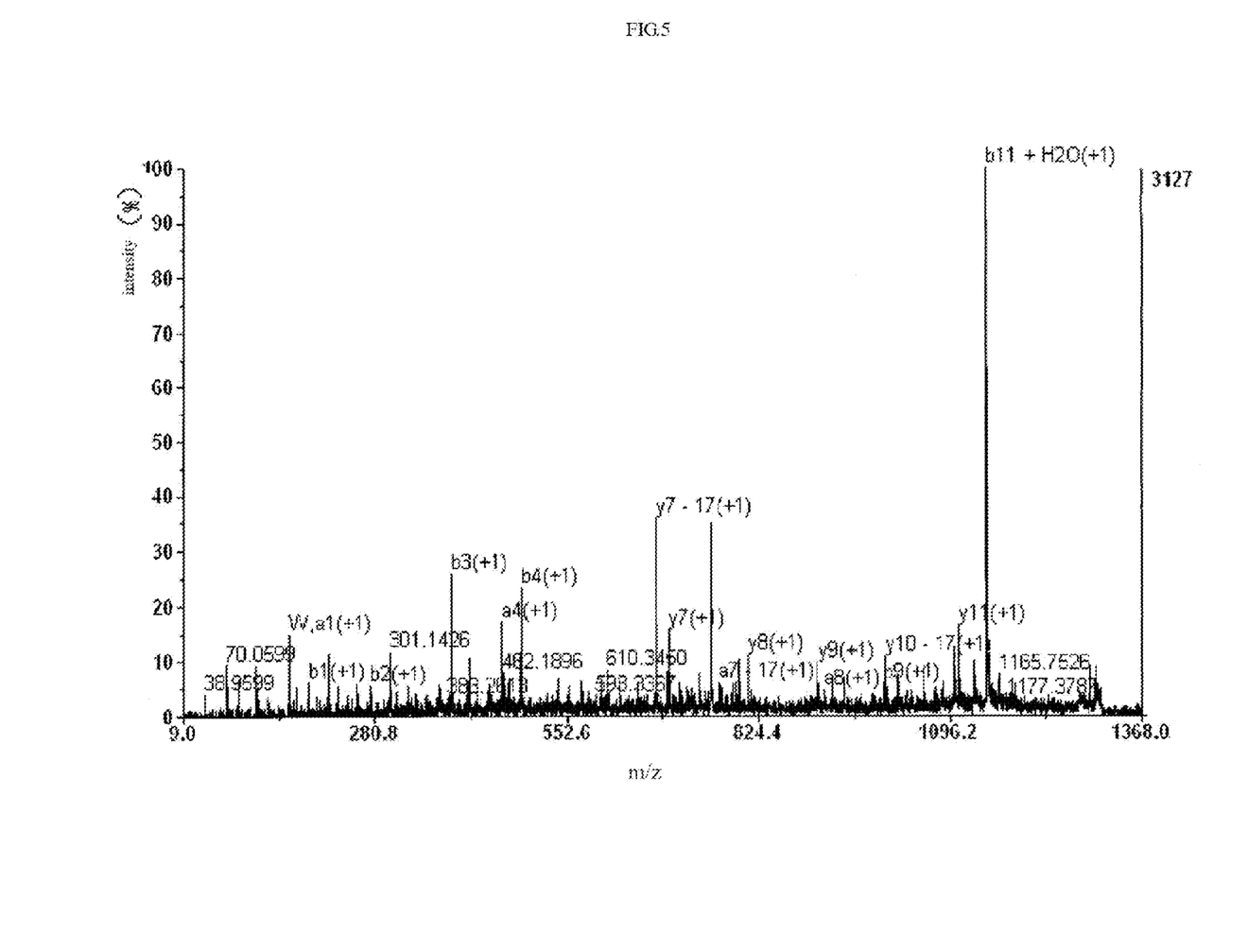
FIG. 5 shows chromatogram map of fraction C.
Figure 6:
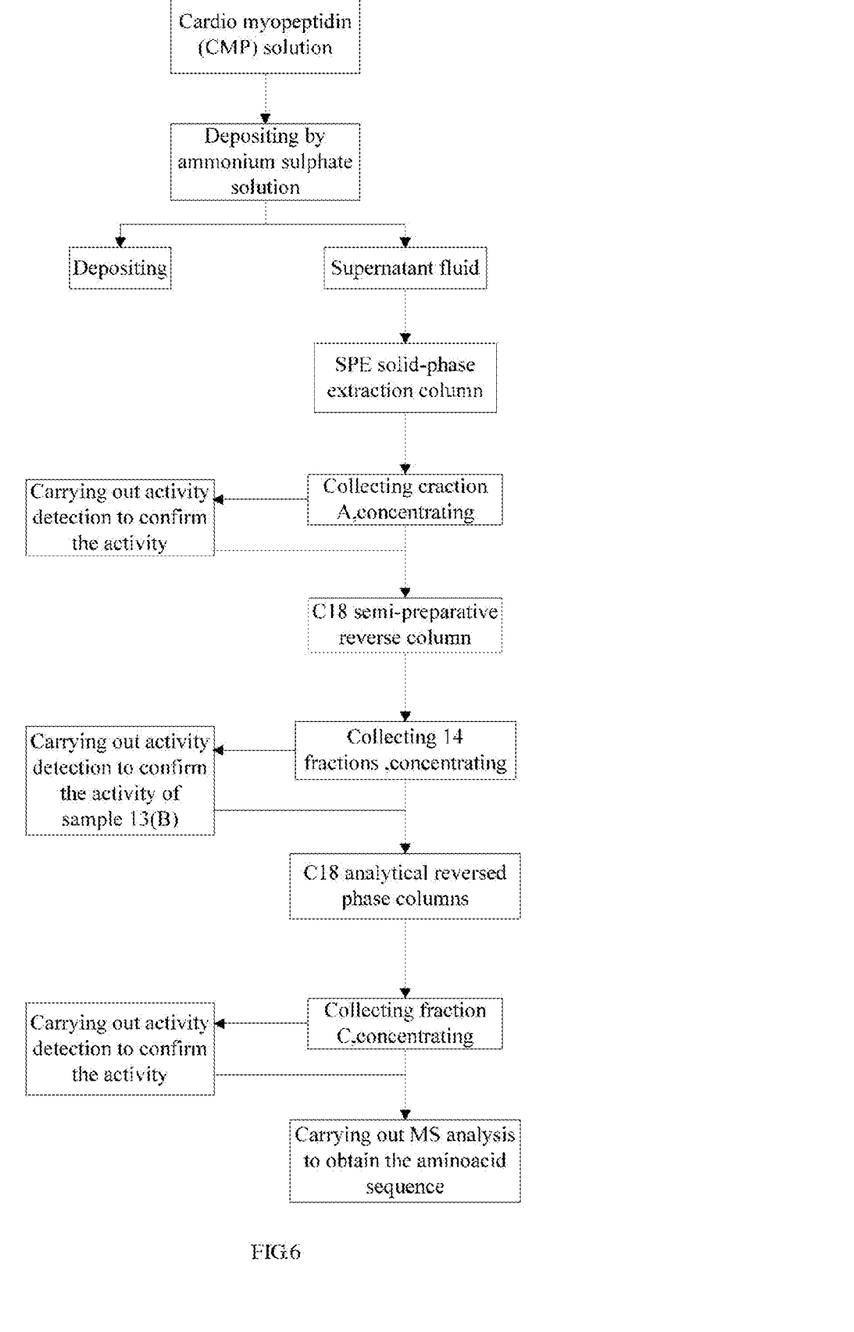
FIG. 6 shows the specific flow chart of the method for extraction of the polypeptide (myopeptidin C)
Figure 7A:
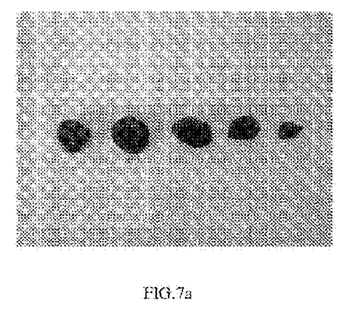
Figure 7B:
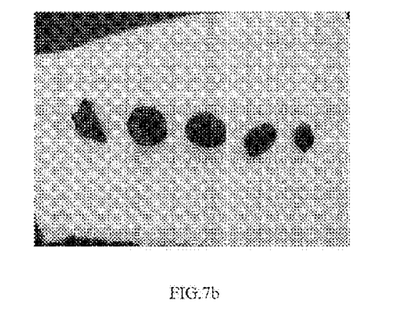
Figure 7C:
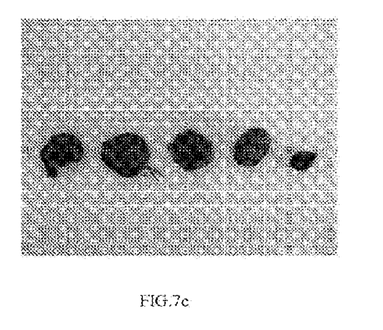
Figure 7D:
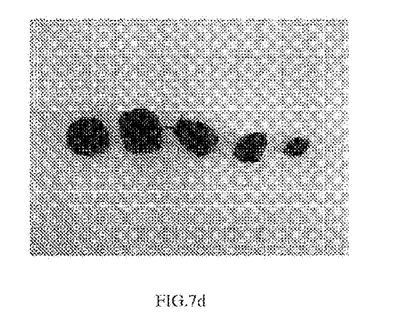
Figure 8A:
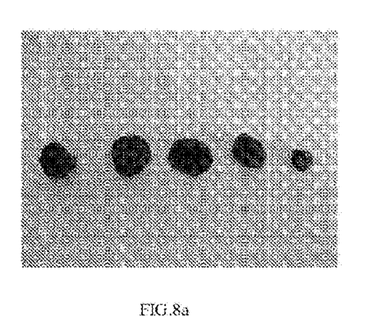
Figure 8B:
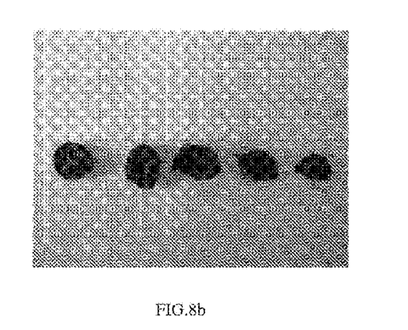
Figure 8C:
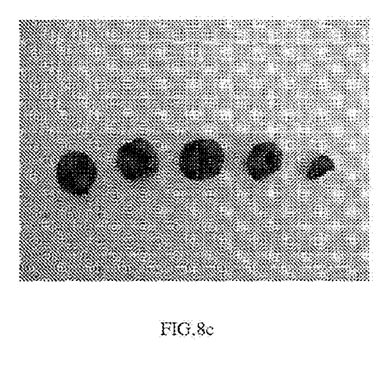
Figure 8D:
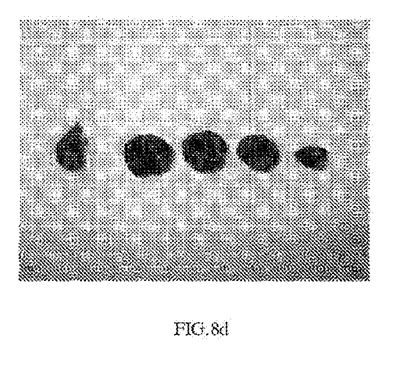

(2) Condition and Method of the Experiment a. adding 70% ammonium sulphate solution to the cardio myopeptidin solution, depositing overnight at 4° C., centrifugating, separating sediment and supernatant fluid;

b. filtering the supernatant fluid by SPE solid phase extraction column, eluting by the mixture of 60% acetonitrile and 0.1% trifluoroacetic acid, collecting fraction A;

c. concentrating the fraction A, isolating by reversion phase preparative chromatography, collecting active fraction B, condition of the reversion phase preparative chromatography is as follows:

mobile phase: A phase is 100% H2O+0.1% TFA, B phase is 60% ACN+0.1% TFA;
ultraviolet detector: wavelength λ=280 nm, R=3.0;
gradient elution: 0~5 Min 0% B, 5~35 min 0%~100% B, 35~40 min 100% B, 40~45 min 100%~0% B.

d. concentrating the active fraction B, further isolating by analytical type reversion phase chromatography, collecting active fraction C;

the condition of analytical type reversion phase chromatography is as follows:

mobile phase: A phase is 100% H2O+0.1% TFA, B phase is 95% ACN+0.1% TFA; ultraviolet detector: wavelength λ=280 nm, R=3.0;
gradient elution: 0~5 min 0% B, 5~50 min 0%~100% B, 50~60 min 100% B, 60~65 min 100%~0% B;

e. detecting the active fraction C by mass spectrometric, identifying that there is amino acid sequence with active polypeptide in active fraction C, as shown in FIGS. 2 and 3.

Example 6

This example relates to structure identification and quality inspection in the process of extracting cardio myopeptidin C from cardio myopeptidin solution.

(1) MS Detection

MALDA-TOF-TOF mass spectrometer (AB company of U.S.-4800) is used for mass spectrometric detection of the product, wherein, MALDA-TOF MS takes positive ion reflective detect mode, MS/MS takes positive ion reflective mode, the results are showed in FIG. 2.

(2) Activity Detection

"Activity detection experiment of cultivation of myocardium cell" provided by DaLian Zhen-Ao Pharmaceutical CO., LTD is adopted in the activity detection. The experiment is based on test of vitro cultured myocardium poisoned by adriamycin, wherein, 2,4-diphenyltetrazolium bromide (MTT) is used as reaction indicator to observe the enhancement of the activity of mitochondria dehydrogenase of the damaged myocardium conducted by cardio myopeptidin, to determine the protective effect of myocardium.

The results of the activity detection are showed as follows:

| Sample No. | original | peptide | peptide | peptide |
|---|---|---|---|---|
| Activity value | 3.2437 | 2.3570 | 2.7328 | 2.564 |

Example 7

This example relates to the use of cardio myopeptidin C (CMPC) for producing the medicament for prevention and/or treatment of myocardial ischemia.

1. EXPERIMENT MATERIAL 1.1 Experiment Animal

Neonatal SD rat, 2~4 days old, provided by Animal Center of Shenyang pharmaceutical university.

SD rat, body weight of 200~300 g, half male and half female, provided by Laboratory Animal Centre of the Chinese People's Liberation Army Academy of Military Medical Sciences, with animal certificate No.: SCXK (military) 2002-001.

1.2 Drug and Reagent

Cardio myopeptidin C (CMPC), provided by DaLian Zhen-Ao Pharmaceutical CO., LTD.

Verapamil injection (Ver): provided by Shanghai Harvest Pharmaceutical CO., LTD, with specification: 2 ml:5 mg, and lot number: 070701;

Doxorubicin injection (adriamycin): provided by Guangdong Shantou Special Zone Meiji Pharmaceutical CO., LTD, with specification: 10 mg/bottle, and lot number: 070702;

DMEM culture medium (high glucose): Gibco, lot number 1290007;

DMEM culture medium (low glucose): Gibco, lot number 1348529;

Collagenase II: Gibco; fetal bovine serum: Tianjin Haoyang Biological Products Science and Technology CO., LTD, lot number 04700701-3100

Methyl thiazolyl tetrazolium (MTT): Amresco; NBT: Amresco, specification: 100 mg Urethane: Tianjin BENCHMARK Chemical Reagent CO., LTD, lot number 20060218;

Superoxide dismutase (SOD), malondialdehyde (MDA), creatine kinase (CK) and lactate dehydrogenase (LDH) reagent kits all purchased from Nanjing Jiancheng Bioengineering Institute, lot number 20080122;

Acetic acid: Tianjin Baishi Chemical Industry CO., LTD, specification: 500 mg, lot number:20070712;

Anhydrous ethanol: Tianjin baishi chemical industry CO., LTD, specification: 500 mg, lot number:20070410.

2. EXPERIMENT METHOD 2.1 In Vitro Experiment
2.1.1 Primary Culture of Myocardium Cell Take ventricle from Neonatal SD rat, wash with D-Hank's and cut to small pieces, digest with collagenase II to obtain the myocardium cell and fibroblast, which are cultivated with high glucose DMEM (dmem-h-15) culture medium containing 15% fetal bovine serum. Remove the fibroblast through differential adhesion and chemistry method, and inoculate myocardium cell on the 96-well plates.

2.1.2 The Against Function of Cmpc to Injury of Adriamycin to Primary Culture Myocardium Cell.

Cell culture method is the same as 2.1.1

Preparation of model: Blank Control Group: cultivating myocardium cell with DMEM-H-15;

Model Group: adding 1 mg/L adriamycin, washing the plate with DMEM-H-15 two times after being cultivated for 1 h, adding DMEM-H-15 for cultivation;

Positive control group (Verapamil 2, 0.4, 0.08 mg/ml) and treating group with drugs of different concentration (CMPC 50, 10, 2, 0.4, 0.08, 0.016, 0.0032, 0.00064 mg/L): washing the plate of myocardium cell damaged by adriamycin for 1 hour with DMEM-H-15 twice, then respectively adding the Verapamil (ver) of different concentration and CMPC (bulk volume of aforementioned every culture system is 100 μl/well, concentration referring to finial concentration). Measuring the activity of mitochondria succinate dehydrogenase of myocardium cell through MTT after continued cultivation for 24 hours, and calculating the protective rate, to figure out EC50.

Protective rate=(Ax−Amodel)/(Acontrol−Amodel)× 100%;

(Ax, Amode, Acontrol respectively represent Absorbance value of Drug administration groups, Model Group and Blank control group.

In Adriamycin Damage Mode, CMPC can improve the survival rate of myocardium cell prominently, and the effect is best when concentration is 0.016~2 mg/L, which is significantly different compared to the Model Group. The CMPC EC50 of plate 1, 2, 3 in the Adriamycin Damage Mode is respectively 0.15, 0.13, 0.27 ml/L. The results are shown in Table 1 (CMPC protective rate for myocardium cell is represent by "%").

TABLE 1

Effect to the survival rate of myocardium cell damaged by adriamycin of CMPC.

| Group | Dosage (mg/L) | Plate 1 A540 | % | Plate 2 A540 | % | Plate 3 A540 | % |
|---|---|---|---|---|---|---|---|
| Blank control group | — | 0.768 ± 0.036 | — | 0.824 ± 0.039 | — | 0.903 ± 0.050 | — |
| Model Group | — | 0.660 ± 0.044## | — | 0.716 ± 0.018# | — | 0.692 ± 0.048 | — |
| CMPC group | 0.0032 | 0.662 ± 0.036 | 2.01 | 0.755 ± 0.033* | 36.17 | — | — |
|  | 0.016 | 0.695 ± 0.039 | 33.08 | 0.755 ± 0.024* | 35.55 | 0.810 ± 0.020** | 55.92 |
|  | 0.08 | 0.703 ± 0.012* | 40.49 | 0.769 ± 0.055* | 49.30 | 0.819 ± 0.016** | 60.35 |
|  | 0.4 | 0.723 ± 0.018** | 58.27 | 0.777 ± 0.057* | 56.11 | 0.781 ± 0.050** | 42.34 |
|  | 2 | 0.690 ± 0.025 | 27.98 | 0.753 ± 0.065 | 33.85 | 0.775 ± 0.008** | 39.42 |
|  | 10 | 0.665 ± 0.032 | 4.79 | 0.752 ± 0.039 | 33.54 | 0.768 ± 0.057* | 36.41 |
|  | 50 | 0.662 ± 0.031 | 2.47 | 0.752 ± 0.036 | 33.08 | 0.756 ± 0.014* | 30.49 |
| Positive Control Group | 0.08 | 0.694 ± 0.110 | 31.53 | 0.749 ± 0.031* | 30.45 | 0.755 ± 0.021* | 30.09 |
|  | 0.4 | 0.714 ± 0.021* | 50.23 | 0.749 ± 0.050 | 30.29 | 0.770 ± 0.012** | 37.28 |
|  | 2 | 0.710 ± 0.099 | 46.83 | 0.767 ± 0.045* | 46.68 | 0.768 ± 0.013** | 36.18 |

Comparing to Model Group, **$P < 0.01$, *$P < 0.05$; Comparing to blank control grou, p **$P < 0.01$, *$P < 0.05$.

2.1.3 Anti-Hypoxia/Reoxygenation Injury Effect of CMPC to Primary Culture Myocardium Cell.

Cell cultivation method is the same as that in 2.1.1

Preparation of model: Preparing the model by using the myocardium cell cultured for 48~72 h, dividing the cell on the culture plate to following groups: Control Group, Model Group, Verapamil Group (2, 0.4, 0.08 mg/l final concentration) and CMPM Group (final concentration of 50, 10, 2, 0.4, 0.08, 0.016, 0.0032 mg/l), 3 wells for every group. Except the Control Group, the other groups are prepared by following method: placing the monolayer myocardium cell on center of culture plate on low glucose medium (containing Verapamil or CMPM with corresponding concentration), then placing the culture plate into the vacuum drying machine, filling nitrogen, and hermetically culturing, causing myocardial injury after oxygen lack for 15 hours, then being cultured for 1 hour by high glucose DMEM medium (95% atmosphere and 5% CO2) to cause reoxygention injury. Measuring the absorbance value at 540 nm by using MTT method, and the same as above, calculating the protective rate to figure out EC50.

In hypoxia/reoxygenation injury model, CMPC can improve the survival rate of myocardium cell significantly, which has best effect on concentration of 0.09~2 mg/L and has significant difference compared to the Model Group. The CMPC EC50 of plate 1, 2, 3 is 0.66, 0.14, 0.82 ml/L respectively. The results are shown in Table 2 (the CMPC protective rate to myocardium cell is represent by %).

TABLE 2

Effect to survival rate of myocardium cell damaged by hypoxia/reoxygenation of cardio myopeptidin.

| Group | Dosage (mg/L) | Plate 1 A540 | % | Plate 2 A540 | % | Plate 3 A540 | % |
|---|---|---|---|---|---|---|---|
| Blank Control Group | — | 0.768 ± 0.036 | — | 0.768 ± 0.036 | — | 0.903 ± 0.050 | — |
| Model Group, | — | 0.484 ± 0.043## | — | 0.485 ± 0.036## | — | 0.737 ± 0.030## | — |
| CMPC | 0.0032 | 0.496 ± 0.031 | 4.11 | 0.543 ± 0.052* | 20.37 | 0.763 ± 0.018 | 15.86 |
| | 0.016 | 0.526 ± 0.032 | 14.69 | 0.550 ± 0.024** | 22.85 | 0.777 ± 0.014* | 24.20 |
| | 0.08 | 0.558 ± 0.025** | 26.09 | 0.622 ± 0.047** | 48.52 | 0.800 ± 0.020** | 38.05 |
| | 0.4 | 0.594 ± 0.043** | 38.95 | 0.599 ± 0.032** | 40.20 | 0.815 ± 0.014** | 47.29 |
| | 2 | 0.566 ± 0.057** | 28.91 | 0.573 ± 0.052** | 30.99 | 0.843 ± 0.032** | 64.26 |
| | 10 | 0.534 ± 0.033* | 17.74 | 0.540 ± 0.026* | 19.36 | 0.790 ± 0.023** | 34.43 |
| | 50 | 0.510 ± 0.030 | 9.05 | 0.536 ± 0.036* | 18.12 | 0.761 ± 0.019 | 14.96 |
| Positive Control Group | 0.08 | 0.524 ± 0.036 | 14.16 | 0.553 ± 0.031** | 23.85 | 0.787 ± 0.020** | 30.62 |
| | 0.4 | 0.541 ± 0.029* | 20.15 | 0.579 ± 0.028** | 33.18 | 0.795 ± 0.022** | 35.44 |
| | 2 | 0.520 ± 0.060* | 12.87 | 0.569 ± 0.029** | 29.63 | 0.805 ± 0.018** | 41.37 |

Comparing to Model Group, **P < 0.01, *P < 0.05; Comparing to Blank Control Group, **P < 0.01, *P < 0.05.

2. EXPERIMENT IN VIVO

2.1. Protective Effect of Preventive Administration of CMPC to Hypoxia/Reoxygenation Injury of Rat's Myocardium Cell.

70 SD rats (250~300 g per rat) were taken, wherein, 60 rats were divided into 6 groups evenly and randomly according to weight, every 10 of each group, the remains are kept for replacement of dead animals of each group.

Normal Control Group: carrying out sham operation, threading a silk suture through the left anterior descending coronary artery (LAD) without ligation;

Model Group: intravenous injecting saline solution of 5 ml/kg 30 minutes before ligation, and the preparation of hypoxia/reoxygenation model is the same as Normal Control Group;

Positive Control Group: intravenous injecting Verapamil of 1 ml/kg 30 min before ligation, preparation of the hypoxia/reoxygenation model is the same as Normal Control Group.

CMPCs high, medium and low dosage group: intravenous injecting CMPC of corresponding concentration (1.8, 0.6, 0.2 mg/kg) 30 min before ligation, preparation of the hypoxia/reoxygenation model is the same as Normal Control Group.

Preparation of the Model:

Intraperitoneal injecting 6% Urethane with 20 ml/kg to anaesthetize the animal, fixing the animal on operating table in supine position; being connected with the electrocardiograph to detect the limb II lead electrocardiogram, tracheal intubating and connecting the animal with respirators, taking continuous positive end-expiratory pressure with tidal volume of 6 ml/200 g, frequency of 55/min and breathing ratio of 2:1. Carrying out thoracotomy on the gap between the forth and the fifth ribs of the left border of sternum, separating the ribs and removing the pericardium. Ligating at the left anterior descending coronary artery by using 6/0 silk suture by the sign of left auricle lower margin, and setting a piece of polyethylene pipe with diameter of 1 mm between the ligation silk suture and blood vessel. Ligating the silk suture to press the left anterior descending coronary artery by the polyethylene pipe and cause myocardial ischemia. Taking part of myocardium becoming grey and electrocardiogram S-T segment raising as the sign of that the left anterior descending coronary artery is ligated successfully. Taking out the polyethylene pipe carefully to cause the reperfusion. Verifying the success of reoxygenation by reactive hyperemia of ischemia area and the descending of the raised S-T segment by ½. Reoxygenation for 30 minutes, then sampling blood from abdominal aorta to prepare serum which is used to measure the biochemical index (measuring the content of CK, LDH, MDA, SPD according to the Reagent kits Instruction).

Rat's heart was taken and after being blooded, the residual blood in the ventricle was cleaned by normal saline to weight the weight of whole heart. Fat was removed, the heart was crosscut into 4~5 pieces and was put into a tube, to be carried out NBT dye at 37° C. (dying the normal tissue rather than the ischemic tissue), taking photographs. The ischemic area of the myocardium was cut to take a weighing, and then the myocardial infarct size (MIS) was calculated by the ratio of weight of the ischemic area of the myocardium to whole heart weight, which was present by percentage.

The activity value of CK, LDH of rat serum was significantly increased (P<0.01) in Model Group, while was significantly declined (P<0.05) in Positive Control Group. The activity value of LDH of rat serum was significantly declined (P<0.05) in CMPC high dosage group, CMPC medium dosage group compared with Model Group; the activity value of CK was significantly declined in CMPC high dosage group, CMPC medium dosage group (P<0.05); the activity value of CK, LDH was declined in CMPC low dosage group without significant difference. The results are shown in Table 3.

TABLE 3

The effect of preventive administration of CMPC to the value of CK, LDH of serum of ischemia/reperfusion damaged rat ($\bar{x} \pm SD$)

| Group | Dosage (mg/kg) | Number (n) | CK (U/ml) | LDH (U/L) |
|---|---|---|---|---|
| Sham Operation Group | — | 9 | 1.632 ± 0.448 | 6971.01 ± 792.23 |
| Model Group | — | 10 | 2.568 ± 0.524## | 8050.00 ± 489.68## |
| Positive Control Group | 1.0 | 10 | 2.087 ± 0.432* | 7376.09 ± 784.64* |
| CMPC high dosage group | 1.8 | 10 | 2.045 ± 0.358* | 7453.80 ± 366.11* |
| CMPC medium dosage group | 0.6 | 11 | 2.172 ± 0.329* | 7531.58 ± 414.64* |
| CMPC low dosage group | 0.2 | 11 | 2.238 ± 0.274 | 7555.34 ± 600.16 |

Comparing to Model Group, **$P < 0.01$, *$P < 0.05$;
comparing to Sham Operation Group, **$P < 0.01$.

The activity of SOD of rat serum was significantly declined ($P<0.01$) in Model Group, while MDA value was raised significantly ($P<0.01$). The positive drug of Ver could significantly raise the SOD activity of serum ($P<0.01$) and decline the activity of MAD ($P<0.05$). Compared with the Model Group, the SOD activity of serum of rat with ligated artery was significantly raised ($P<0.01$, $P<0.05$) in CMPC-H, M, L group, while MDA was declined ($P<0.01$, $P<0.05$). The results are shown in Table 4.

TABLE 4

The effect of preventive administration of CMPC to the value of SOD, MDA of serum of ischemia/reperfusion damaged rat ($\bar{x} \pm SD$)

| Group | Dosage (mg/kg) | Number (n) | SOD (U/ml) | MDA (nmol/ml) |
|---|---|---|---|---|
| Sham Operation Group | — | 9 | 132.61 ± 5.65 | 4.275 ± 0.813 |
| Model Group | — | 10 | 113.98 ± 18.63## | 5.483 ± 0.832## |
| Positive Control Group | 1.0 | 10 | 135.63 ± 7.878** | 4.755 ± 0.718* |
| CMPC high dosage group | 1.8 | 8 | 135.67 ± 8.64** | 4.371 ± 0.47** |
| CMPC medium dosage group | 0.6 | 11 | 130.43 ± 10.55* | 4.847 ± 0.570 |
| CMPC low dosage group | 0.2 | 11 | 134.85 ± 12.55** | 4.642 ± 0.978* |

Comparing to Model Group, **$P < 0.01$, *$P < 0.05$;
comparing to Sham Operation Group, **$P < 0.01$.

Myocardial infarction size was raised significantly in Model Group ($P<0.01$). Compared with Model Group, the myocardial infarction size of rat was significantly declined in the Positive Control Group and CMPC group. The results are shown in Table 5 and FIG. 7.

TABLE 5

The effect of preventive administration of CMPC to the myocardial infarction size of ischemia/reperfusion damaged rat ($\bar{x} \pm SD$)

| Group | Dosage (mg/kg) | Number (n) | MIS (%) |
|---|---|---|---|
| Sham Operation Group | — | 9 | 0 |
| Model Group | — | 10 | 6.68 ± 1.72## |
| Positive Control Group | 1.0 | 12 | 4.19 ± 0.70** |
| CMPC high, dosage group | 1.8 | 8 | 3.47 ± 1.08** |
| CMPC medium dosage group | 0.6 | 11 | 4.17 ± 0.62** |
| CMPC low dosage group | 0.2 | 11 | 4.67 ± 0.74** |

Comparing to Model Group, **$P < 0.01$, *$P < 0.05$;
comparing to Sham Operation Group, ##$P < 0.01$.

2.2 The Protective Function of CMPC Therapeutic Administration to Hypoxia/Reoxygenation Injured Myocardium Cell of Rat.

The drug was intravenously injured on the tail 5 minutes after ligation of LAD, then reperfusion was carried out for 30 min 30 minutes after ligation of LAD. Heart was taken after sampling blood from abdominal aorta. The biochemical index and the myocardial infarction size were measure by using the above method.

The values of CK and LDH of serum of rat were significantly raised in Model Group ($P<0.01$). The activity of CK and LDH was significantly declined by positive drug of Ver ($P<0.05$, $P<0.01$). The activity of CK and LDH of serum of rat was significantly declined in CMPC high, medium dosage group compared with that in Model Group ($P<0.01$, $P<0.05$). The activity of LDH and CK decline could be reduced in CMPC low dosage group without significant difference. The results are shown in Table 6.

TABLE 6

The effect of therapeutic administration of CMPC to the value of CK, LDH of serum of ischemia/reperfusion damaged rat ($\bar{x} \pm SD$)

| Group | Dosage (mg/kg) | Number (n) | CK (U/ml) | LDH (U/L) |
|---|---|---|---|---|
| Sham Operation Group | — | 8 | 1.378 ± 0.458 | 5986.84 ± 1084.21 |
| Model Group | — | 10 | 2.276 ± 0.529## | 8029.35 ± 685.01## |
| Positive Control Group | 1.0 | 10 | 1.777 ± 0.389* | 6791.96 ± 570.85** |
| CMPC high dosage group | 1.8 | 10 | 1.707 ± 0.332** | 7233.69 ± 297.69** |
| CMPC medium dosage group | 0.6 | 11 | 1.748 ± 0.573* | 7034.59 ± 1167.17* |
| CMPC low dosage group | 0.2 | 11 | 2.026 ± 0.532 | 7763.83 ± 770.70 |

Comparing to Model Group, **$P < 0.01$, *$P < 0.05$;
comparing to Sham Operation Group, **$P < 0.01$.

The SOD activity of rat serum was significantly declined in Model Group ($P<0.05$), while MDA was raised significantly ($P<0.01$). The SOD activity of serum could be raised significantly ($P<0.05$) by the positive drug of Ver, and the activity of MAD was declined ($P<0.05$). Compared with that in the Model Group, the activity of SOD was significantly raised ($P<0.05$, $P<0.01$) in CMPC-H and CMPC-M groups. There was a tendency of raising the SOD activity in CMPC-L group, without significant difference ($P>0.05$) compared with Model Group. The content of MDA could be declined in CMPC-H, CMPC-M and CMPC-L group ($P<0.05$). The results are shown in Table 7.

TABLE 7

The effect of therapeutic administration of CMPC to the value of SOD, MDA of serum of ischemia/reperfusion damaged rat ($\bar{x} \pm SD$)

| Group | Dosage (mg/kg) | Number (n) | SOD (U/ml) | MDA (nmol/ml) |
|---|---|---|---|---|
| Sham Operation Group | — | 8 | 145.35 ± 10.60 | 4.395 ± 0.693 |
| Model Group | — | 10 | 123.17 ± 20.86# | 5.556 ± 0.813## |
| Positive Control Group | 1.0 | 10 | 140.36 ± 14.00* | 4.960 ± 0.338* |
| CMPC high dosage group | 1.8 | 10 | 143.41 ± 12.14* | 4.685 ± 0.714* |
| CMPC medium dosage group | 0.6 | 11 | 145.41 ± 10.56** | 4.862 ± 0.468* |
| CMPC low dosage group | 0.2 | 11 | 140.59 ± 20.28 | 4.878 ± 0.430* |

Comparing to Model Group, **$P < 0.01$, *$P < 0.05$;
comparing to Sham Operation Group, **$P < 0.01$.

Myocardial infarction size was significantly raised in Model Group ($P<0.01$). Compared with that in Model Group, the myocardial infarction size of rat was significantly declined ($P<0.05$) in Positive Control Group and CMPC group. The results are shown in Table 8 and FIG. 8.

TABLE 8

The effect of therapeutic administration of CMPC to the myocardial infarction size of ischemia/reperfusion damaged rat ($\bar{x} \pm SD$)

| Group | Dosage (mg/kg) | Number (n) | MIS (%) |
|---|---|---|---|
| Sham Operation Group | — | 8 | 0 |
| Model Group | — | 10 | 5.89 ± 1.29## |
| Positive Control Group | 1.0 | 12 | 4.07 ± 1.56** |
| CMPC high dosage group | 1.8 | 11 | 3.68 ± 1.39** |
| CMPC medium dosage group | 0.6 | 11 | 4.20 ± 0.78** |
| CMPC low dosage group | 0.2 | 11 | 3.95 ± 0.97** |

Comparing to Model Group, **$P < 0.01$, *$P < 0.05$;
comparing to Sham Operation Group, **$P < 0.01$.

3. CONCLUSION

CMPC could raise the activity of mitochondria dehydrogenase of the injured myocardial cell, and had some protective function to the injured myocardial cell in the model of primary culture myocardium cell of neonatal rat which was injured by adriamycin and hypoxia/reoxygenation. preventive and therapeutic administration of CMPC could significantly declines the content of CK, LDH and MDA of serum of rat injured by ischemia/reperfusion, and raises the content of SOD with some dose-dependence, as well as could declines the myocardial infarction size, which indicates that CMPC preventive and therapeutic administration had protective function to the myocardial cell of ischemia/reperfusion injured rat.

The invention claimed is:

1. A method for extracting the polypeptide of SEQ ID NO:2 from a cardio myopeptidin-containing solution, comprising steps of:
   (1) adding an ammonium sulphate solution to the cardio myopeptidin-containing solution, depositing, centrifugating, separating supernatant fluid and sediment;
   (2) filtrating the supernatant fluid by solid phase extraction tube with an organic solvent as eluent, collecting fraction A;
   (3) concentrating the fraction A, then isolating the concentrated fraction A by reversion phase preparative chromatography, collecting fraction B;
   (4) concentrating the fraction B, then further isolating the concentrated fraction B by analytical type reversion phase chromatography, collecting fraction C; and
   (5) detecting the fraction C with mass spectrometric detection to identify amino acid sequence of the polypeptide in fraction C by MS data analysis, the fraction C being the polypeptide.

2. The method according to claim 1, wherein a weight percent concentration of the ammonium sulphate solution is 60 to 80%.

3. The method according to claim 1, wherein the organic solvent in step (2) is a mixture comprising acetonitrile 60% and trifluoroacetic acid 0.1%.

4. The method according to claim 1, wherein in step (3), the fraction A is concentrated to ⅛~¾ of an original volume, and conditions of the reversion phase preparative chromatography are: mobile phase: A phase being 100% $H_2O$+0.1% TFA, B phase being 60% ACN+0.1% TFA; ultraviolet detector: wavelength k=280 nm, R=3.0; gradient elution: 0~5 Min 0% B, 5~35 min 0%~100% B, 35~40 min 100% B, 40~45 min 100%~0% B.

5. The method according to claim 1, wherein in step (4), the fraction B is concentrated to ⅛~½ of an original volume, and conditions of further separation by using the analytical type reversion phase chromatography are: mobile phase: A phase being 100% $H_2O$+0.1% TFA, B phase being 95% ACN+0.1% TFA; ultraviolet detector: wavelength λ=280 nm, R=3.0; gradient elution: 0~5 Min 0% B, 5~50 min 0%~100% B, 35~40 min 100% B, 40~45 min 100%~0% B.

6. A chemical synthesis method of the polypeptide of SEQ ID NO:2, wherein the method comprises steps of:
   (1) protecting an amino-group of tryptophane, serine, aspartic acid, valine, leucine, arginine, glycine, methionine, alanine, phenylalanine and lysine by using a protecting group for the amino-group respectively;
   (2) swelling a solid phase carrier, reacting a first protected amino acid of SEQ ID NO: 2 onto the solid phase carrier, then rinsing the resulting product, obtaining a solid phase carrier bearing the first protected amino acid;
   (3) removing the protecting group for the amino-group from the first protected amino acid in the solid phase carrier obtained in step (2);
   (4) combining a second amino acid of SEQ ID NO: 2 in the presence of a condensating agent, with the solid phase carrier obtained in step (3) to form a dipeptide linkage, then removing the protecting group for the amino-group from the second amino acid, rinsing to obtain the solid phase carrier bearing the dipeptide linkage;
   (5) according to the amino acid sequence of SEQ ID NO: 2, adding corresponding protected amino acid in turn, repeating the steps of removing the amino group protecting group and rinsing to extend the peptide chain until the last amino acid is linked to the peptide chain;
   (6) immersing the solid phase carrier prepared in step (5) in a soak solution, then filtering and depositing the filtrate to obtain a coarse polypeptide; and
   (7) isolating and purifying the coarse polypeptide to obtain the polypeptide of SEQ ID NO:2.

7. A chemical synthesis method according to claim 6, wherein in step (1), the amino-group is protected by one of following groups:
   (1) carbobenzoxyl;
   (2) t-butyloxycarbonyl;
   (3) tosyl; or
   (4) fmoc.

8. A method for treating ischemia of tissue and organ, comprising administering to a subject in need thereof the polypeptide of SEQ ID NO:2.

9. The method of claim 8, which is a method for treating myocardial ischemia, cerebral ischemia, hepatic ischemia, intestines ischemia, stomach ischemia, lung ischemia or nephridium ischemia.

10. The method of claim 8, which is a method for treating myocardial ischemia.

11. The method according to claim 2, wherein the weight percent concentration of the ammonium sulphate solution is 70%.

12. A chemical synthesis method of the polypeptide of SEQ ID NO:1, wherein the method comprises steps of:
   (1) protecting an amino-group of tryptophane, serine, aspartic acid, valine, leucine, arginine, glycine, methionine, alanine, phenylalanine and lysine by using a protecting group for the amino-group respectively;
   (2) swelling a solid phase carrier, reacting a first protected amino acid of SEQ ID NO:1 onto the solid phase carrier, then rinsing the resulting product, obtaining a solid phase carrier bearing the first protected amino acid;
   (3) removing the protecting group for the amino-group from the first protected amino acid in the solid phase carrier obtained in step (2);
   (4) combining a second amino acid of SEQ ID NO:1 in the presence of a condensating agent, with the solid phase carrier obtained in step (3) to form a dipeptide linkage, then removing the protecting group for the amino-group from the second amino acid, rinsing to obtain the solid phase carrier bearing the dipeptide linkage;
   (5) according to the amino acid sequence of SEQ ID NO:1, adding corresponding protected amino acid in turn, repeating the steps of removing the amino group protecting group and rinsing to extend the peptide chain until the last amino acid is linked to the peptide chain;
   (6) immersing the solid phase carrier prepared in step (5) in a soak solution, then filtering and depositing the filtrate to obtain a coarse polypeptide; and
   (7) isolating and purifying the coarse polypeptide to obtain the polypeptide of SEQ ID NO:1.

* * * * *

SEQUENCE LISTING

```
<160> NUMBER OF SEQ ID NOS: 2

<210> SEQ ID NO 1
<211> LENGTH: 12
<212> TYPE: PRT
<213> ORGANISM: Artificial Sequence
<220> FEATURE:
<223> OTHER INFORMATION: cardio myopeptidin X

<400> SEQUENCE: 1

Trp Ser Asn Val Leu Arg Gly Met Gly Gly Ala Phe
1               5                   10

<210> SEQ ID NO 2
<211> LENGTH: 15
<212> TYPE: PRT
<213> ORGANISM: Artificial Sequence
<220> FEATURE:
<223> OTHER INFORMATION: cardio myopeptidin C

<400> SEQUENCE: 2

Lys Gly Ala Trp Ser Asn Val Leu Arg Gly Met Gly Gly Ala Phe
1               5                   10                  15
```